United States Patent [19]

Sahatjian et al.

[11] Patent Number: 5,135,516
[45] Date of Patent: Aug. 4, 1992

[54] LUBRICIOUS ANTITHROMBOGENIC CATHETERS, GUIDEWIRES AND COATINGS

[75] Inventors: Ronald Sahatjian, Lexington, Mass.; Kurt Amplatz, St. Paul, Minn.

[73] Assignee: Boston Scientific Corporation, Watertown, Mass.

[21] Appl. No.: 451,507

[22] Filed: Dec. 15, 1989

[51] Int. Cl.⁵ .................... A61M 5/32; A61M 25/00; A61K 9/00; B05D 7/22
[52] U.S. Cl. .................................. 604/265; 604/266; 427/2; 427/230; 427/412.1
[58] Field of Search .................. 604/266, 265; 427/2, 427/230, 412.1

[56] References Cited

U.S. PATENT DOCUMENTS

| | | |
|---|---|---|
| 2,329,456 | 8/1955 | Campbell . |
| 2,911,321 | 11/1959 | Herrmann . |
| 3,005,728 | 10/1961 | Bridgeford . |
| 3,023,126 | 2/1962 | Underwood . |
| 3,092,512 | 6/1963 | Magat . |
| 3,198,692 | 8/1965 | Bridgeford . |
| 3,216,983 | 11/1965 | Shalanski . |
| 3,304,353 | 10/1972 | Harauteneian . |
| 3,457,098 | 4/1986 | Leininger . |
| 3,566,874 | 5/1974 | Shepard . |
| 3,634,123 | 1/1972 | Eriksson . |
| 3,695,921 | 5/1974 | Shepard . |
| 3,810,781 | 6/1976 | Eriksson . |
| 3,812,071 | 6/1974 | Stoy et al. . |
| 3,844,989 | 11/1974 | Harumiya et al. . |
| 3,846,353 | 11/1975 | Grotta . |
| 3,861,396 | 1/1975 | Vaillancourt . |
| 3,935,342 | 1/1976 | Lim . |
| 3,975,350 | 8/1976 | Hudgin et al. . |
| 4,020,216 | 4/1977 | Miller . |
| 4,026,296 | 5/1977 | Stoy et al. . |
| 4,055,682 | 10/1977 | Merrill . |
| 4,078,015 | 8/1978 | Leitheiser . |
| 4,100,309 | 7/1978 | Micklus . |
| 4,116,898 | 9/1978 | Dudley . |
| 4,118,485 | 10/1978 | Eriksson . |
| 4,119,094 | 10/1978 | Micklus . |
| 4,143,423 | 5/1979 | Sternlieb . |
| 4,145,513 | 3/1979 | Dalibor . |
| 4,156,067 | 5/1979 | Gould . |
| 4,175,161 | 11/1979 | Fogle . |
| 4,267,295 | 5/1981 | Gallop et al. . |
| 4,298,002 | 11/1981 | Ronel . |

(List continued on next page.)

FOREIGN PATENT DOCUMENTS

| | | |
|---|---|---|
| 1215597 | 12/1986 | Canada . |
| 0014238 | 11/1979 | European Pat. Off. . |
| 0093093 | 11/1983 | European Pat. Off. . |
| 0093094 | 11/1983 | European Pat. Off. . |
| 149693 | 1/1985 | European Pat. Off. . |
| 166998 | 1/1986 | European Pat. Off. . |
| 0184684 | 6/1986 | European Pat. Off. . |
| 0217771 | 4/1987 | European Pat. Off. . |
| 2321086 | 11/1974 | Fed. Rep. of Germany . |
| 73701 | 6/1987 | Finland . |
| 49008583 | 6/1944 | Japan . |
| 51000194 | 11/1948 | Japan . |
| 53006430 | 4/1950 | Japan . |
| 55035650 | 6/1950 | Japan . |
| 57031868 | 12/1953 | Japan . |
| 57119756 | 12/1953 | Japan . |
| 58105759 | 7/1954 | Japan . |

(List continued on next page.)

OTHER PUBLICATIONS

Amplatz, "A New Simple Test for Thrombogenicity", *Radiology*, 120: 53-55, Jul., 1976.

(List continued on next page.)

*Primary Examiner*—V. Millin
*Attorney, Agent, or Firm*—Fish & Richardson

[57] ABSTRACT

Method for rendering a preformed article lubricious and antithrombogenic and a device being the same. On the surface of the article a thin coating of a biologically compatible, lubricious, hydrophilic polymer including acid groups, is provided. On the coating, ammonium cation, and heparin are applied in the manner that heparin is bound by electrostatic attraction to the ammonium cation of the coating to permit time release of heparin. A buffer solution may be applied in a manner to act to enhance the lubriciousness of the coating.

48 Claims, 4 Drawing Sheets

U.S. PATENT DOCUMENTS

| | | |
|---|---|---|
| 4,318,947 | 3/1982 | Joung . |
| 4,326,532 | 12/1982 | Hammar . |
| 4,349,467 | 2/1983 | Williams et al. . |
| 4,369,229 | 1/1983 | Shah . |
| 4,373,009 | 2/1983 | Winn . |
| 4,405,773 | 4/1983 | Loshaek . |
| 4,417,892 | 11/1983 | Meisch . |
| 4,430,458 | 2/1984 | Tighe . |
| 4,434,797 | 3/1984 | Silander . |
| 4,459,317 | 7/1984 | Lambert . |
| 4,459,318 | 7/1984 | Hyans . |
| 4,487,808 | 12/1984 | Lambert . |
| 4,515,593 | 5/1985 | Norton . |
| 4,516,970 | 5/1989 | Kaufman . |
| 4,585,666 | 4/1986 | Lambert . |
| 4,589,873 | 5/1986 | Schwartz . |
| 4,642,267 | 2/1987 | Creasy . |
| 4,666,437 | 5/1987 | Lambert . |
| 4,670,313 | 8/1987 | Saudagar . |
| 4,678,671 | 7/1987 | Feijen . |
| 4,690,844 | 9/1987 | Saudagar . |
| 4,729,914 | 3/1988 | Kliment . |
| 4,755,379 | 7/1988 | Jozefonvicz . |
| 4,838,876 | 6/1989 | Wong . |
| 5,091,205 | 2/1992 | Fan . |

FOREIGN PATENT DOCUMENTS

| | | |
|---|---|---|
| 58206753 | 8/1954 | Japan . |
| 57014358 | 11/1958 | Japan . |
| 61168365 | 2/1959 | Japan . |
| 503507 | 5/1973 | Japan . |
| 49-132219 | 12/1973 | Japan . |
| 7503507 | 11/1975 | Japan . |
| 480555946 | 10/1987 | Japan . |
| 1600963 | 10/1981 | United Kingdom . |
| 2112646 | 7/1983 | United Kingdom . |
| 2128500 | 5/1984 | United Kingdom . |
| 2122510 | 6/1984 | United Kingdom . |
| 2163436 | 2/1986 | United Kingdom . |
| 2190387 | 8/1986 | United Kingdom . |
| 7900638 | 9/1979 | World Int. Prop. O. . |
| 8603127 | 4/1986 | World Int. Prop. O. . |
| 8706007 | 3/1987 | World Int. Prop. O. . |
| 8707156 | 10/1987 | World Int. Prop. O. . |

OTHER PUBLICATIONS

Amplatz, "A Simple Non-Thrombogenic Coating", *Investigative Radiology*, vol. 6, Jul.-Aug., 1971, p. 280.

Anderson, "Anticoagulation Techniques for Angiography", *Radiology*, 111: 573-576, Jun. 1974.

Cramer, "A Preliminary Human Study with a Simple Non-Thrombogenic Catheter", *Radiology*, vol. 100, Jul.-Sep., 1971, p. 421.

Cramer, "Reduction of the Surgical Complication Rate by the Use of a Hypothrombogenic Catheter Coating", *Diagnostic Radiology*, vol. 109, Oct.-Dec., 1973, p. 585.

Durst, "Flow Cell Evaluation of Nonthrombogenic Materials", *Radiology*, 106: 507-511, Mar. 1973.

Esquivel, "Reduced Thrombogenic Characteristics of Expanded Polytetrafluoroethylene and Polyurethance Arterial Graphs After Heparin Bonding", *Surgery*, vol. 95, Jan., 1984, p. 102.

Frech, "A Simple Noninvasive Technique to Test Nonthrombogenic Surfaces".

Linhardt, "Differential Anticoagulant Activity of Heparin Fragments Prepared Using Microbial Heparinase", *J. Biological Chemistry*, vol. 257, No. 13, Jul. 1982, p. 7310.

McCarty, "Thrombogenicity of Guidewires", *The American Journal of Cardiology*, vol. 32, Dec. 1973, p. 943.

Miyam et al., "A New Antithrombogenic Heparinized Polymer", *J. Bio. Med. Mater. Res.*, vol. 11, p. 251, 1977.

Mori et al., "The Effect of Released Heparin from the Heparinized Hydrophilic Polymer (HRSD) on the Process of Thrombus Formation", Trans. Am. Soc. Artif. Intern. Organs, vol. XXIV, p. 736, 1978.

Nichols, "Effect of Heparin Bonding on Catheter Induced Fibrin Formation and Platelet Activation", *Circulation*, 70, No. 5, 843-850, 1984.

Noishiki et al., "Prevention of Thrombosis-Related Complications in Cardiac Catheterization and Angiography Using Heparinized Catheter, (Anthron)", *ASAIO*, vol. 10(3), Jul.-Sep. 1987, p. 359.

Ovitt, "Guidewire Thrombogenicity and its Reduction", *Radiology*, 111: 43-46, Apr., 1974.

Roberts, "Thrombogenicity of Arterial Catheters and Guidewires," *British Journal of Radiology*, vol. 50, p. 415, 1977.

Abstracts from Circulation, vol. 62, Supp. III, OCt., 1980.

Anderson, "A Scanning Electron Microscope Study of Angiographic Catheters and Guidewires", *Radiology*, 111: 567-571, Jun. 1974.

Haut, "Complication Rates of Transfemoral and Transaortic Catheterization", *Surgery*, vol. 63, No. 4, Apr. 1968, p. 594.

Horbit, "Absorption of Proteins from Plasma to a Series of Hydrophillic-Hydrophobic Copolymers I Analysis with the In Situ Radioiodination Technique", *J. of Biomedical Materials Research*, vol. 15, p. 403 (1981).

Klarscov, "Catheter-Associated Bacteriuria", *Acta. Obstet. Gynecol. Scanned*, 65:295-299, 1986.

Lipton, "Evaluation of Catheter Thrombogenicity In Vivo with Indium Labelled Platelets", *Radiology*, 135:191-194, Apr., 1980.

Nishi, "Complex-Forming Poly(Oxyethylene) Poly (acrylic acid) Interpenetrating Polymer Networks, I. Preparation, Structure and Physco Elastic Properties", *Macromolecules*, vol. 18, No. 8, 1985, p. 1519.

Okano, "Effect of Hydrophilic and Hydrophobic Microdomains on Mode of Interaction Between Block Polymer and Blood Platelets", *Journal of Biomedical Materials Research*, vol. 15, p. 393, 1981.

Ramsay, "An Experimental Study of Hydrophilic Plastics for Urological Use", *British Journal of Urology*, 1986, 58, p. 70.

Shook, "Everting (toposcopic) Catheter for Broad Clinical Application", *Transactions of the ASME*, vol. 108, May 1986, p. 168.

Takayasu, "Plastic-Coated Guidewire for Hepatic Arteriography," *Radiology*, vol. 66, No. 2, p. 545.

Tidd, "Comparison of Hydrophillic Polymer-Coated Latex, Uncoated Latex, and PVC in Swelling Balloon Catheters in the Prevention of Urinary Infection", *British J. of Urology*, 1976, p. 285.

Theodore, "A Convenient Preparation of Acrylic-Urethan Nonaqueous Dispersions", Journal of Coatings Technology.

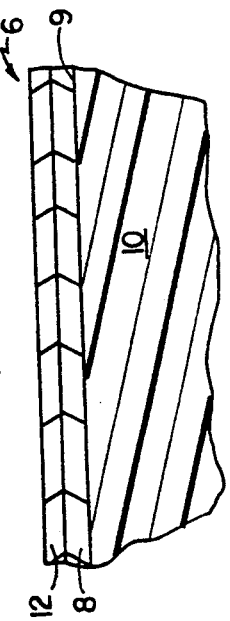
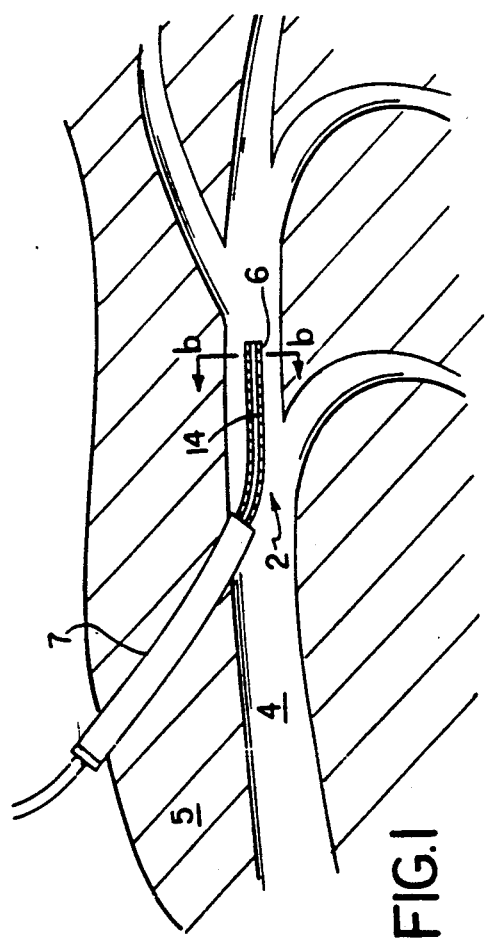
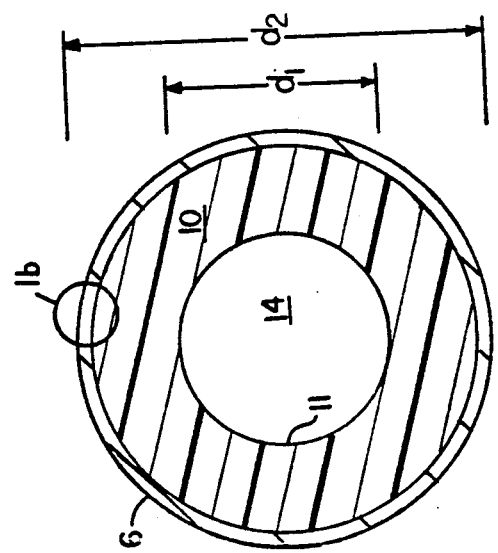

LUBRICIOUS ANTITHROMBOGENIC CATHETERS, GUIDEWIRES AND COATINGS

BACKGROUND OF THE INVENTION

Field of the Invention

This invention relates to antithrombogenic and lubricious medical instruments such as catheters and guidewires useful, e.g. in angiography.

Contacting blood with a foreign object having a plastic or metal surface induces a complex set of clot-forming reactions that occur at the blood surface interface. Thromboembolism is a major complication associated with the clinical use of artificial devices, such as catheters, guidewires, mechanical heart valves, ventricular assist devices, implantable artificial hearts, vascular grafts, etc. In particular, thromboembolism is an important complication of angiographic procedures, particularly with catheter and guidewire manipulations proximal to the brachiocephalic vessels.

Angiographic guidewires are known to be thrombogenic. If a stainless steel or teflon-coated guidewire is exposed to streaming arterial blood in dogs, they are covered by a fibrin sheath within several minutes. It has been suggested that this high degree of thrombogenicity may also be related to the corrugated shape of the guidewires which probably induces turbulence between each wire coil, facilitating platelet adherence. Teflon ® coatings on guidewires, however, offer insufficient protection from thrombogenesis.

Certain agents, for example, heparin, on a foreign surface can inhibit clot formation. Frech et al., in "A Simple Noninvasive Technique to Test Nonthrombogenic Surfaces," *The American Journal of Roentgenology Radium Therapy and Nuclear Medicine*, Vol. 113, 1971, P. 765 discloses coating of a guidewire with a benzalkonium-heparin complex. Ovitt et al., in "Guidewire Thrombogenicity and Its Reduction" *Radiology*, reports Teflon ®-coated guidewires treated with benzalkonium-heparin. Williams U.S. Pat. No. 4,349,467 applies heparin to solid polymeric resin substrates by steeping the substrate in a solution of an ammonium salt and contacting the substrate with a heparin salt solution.

It is also desirable to provide a highly lubricious coating to medical instruments and especially to those instruments that must pass through narrow, tortuous body passages. It has been shown that water soluble polymers which are swellable with water but do not dissolve have very low coefficients of friction when wet, even lower than that of Teflon ® (polytetra fluorethylene).

SUMMARY OF THE INVENTION

The invention features a method for rendering a surface of a preformed article lubricious and antithrombogenic and a medical device for use within the body formed of a base material and having a lubricious coating on its surface. The coating is also capable of reducing the thrombogenicity of the surface.

In one aspect, the method features providing on the surface of the article a thin coating of a biologically compatible, lubricious, hydrophilic polymer including acid groups, and thereafter applying to the coating ammonium cation, heparin and a buffer solution, in the manner that heparin is bound by electrostatic attraction to the ammonium cation of the coating to permit time release of heparin, and the buffer solution acts to enhance the lubriciousness of the coating.

In another aspect, the method features providing on the surface of the article a thin coating of a biologically compatible, lubricious, hydrophilic polymer including acid groups, and thereafter applying to the coating ammonium cation and heparin in the manner that heparin is bound by electrostatic attraction to the ammonium cation of the coating to permit time release of heparin. The thickness of the lubricious and antithrombogenic coating is of the order of about 10 microns or less when dry.

The method may include applying to the lubricious polymer coating ammonium cation and heparin, and thereafter applying the buffer solution. The ammonium cation ma also be applied before the heparin is applied.

The method may also include applying to the lubricious polymer coating ammonium cation, applying buffer solution and thereafter applying heparin.

The method may also include applying to the lubricious polymer coating the buffer solution and thereafter applying ammonium cation and heparin.

In various embodiments, the ammonium cation is provided by applying an aqueous solution. The method may include; drying the polymer coating after applying the ammonium cation; drying the coating before providing the buffer solution; selecting a sodium bicarbonate buffer; applying the buffer solution to enhance lubriciousness by the formation of salts of the acid groups; providing the lubricious polymer may include providing to the surface a primer solution including isocyanate and providing a hydrophilic polymer to the isocyanate. The coefficient of friction of the coating after applying the buffer solution may be less than about 0.1; the hydrophilic polymer may have a molecular weight from about 200,000 to 5,000,000 and be selected from polyacrylic acid, crotonic acid, maleic acid and amino acids and their derivatives and copolymers; the preformed surface may be formed of nylon, polyurethane, polyester, "C-Flex", "Percuflex", "Kraton" or polyethylene; the ammonium cation may be the benzalkonium cation formed by dissociation of benzalkonium chloride; ammonium cation may be provided in a manner causing reaction of cation with the acid groups to form ammonium salts; the ammonium cation and heparin may be applied in the manner to provide a coating which is about 1.0 to 10 microns thick when dry; the coating may be about 2 to 5 micrpns thick when dry; the thickness of the coating may increase by about six to ten times when wet; the thickness of the coating may be about 20 microns when wet; the coating may be applied to an angioplasty catheter; the coating may be applied to an angioplasty balloon catheter; the coating may be applied to a guidewire, a polymer coated guidewire, and other devices used in the vascular system.

In one aspect, the device includes a lubricious, hydrophilic, swellable polymer, being bonded to a surface and having acid groups, ammonium cations, and heparin electrostatically bound to the ammonium cations in a manner permitting time release. The thickness of the lubricious and antithrombogenic coating is of the order of 10 microns or less when dry.

In another aspect, the device includes a lubricious, hydrophilic, swellable polymer bonded to a surface and having acid groups, ammonium cations, and heparin electrostatically bound to the ammonium cations in a manner to permit time release, and acid salts to enhance lubricity.

In various embodiments, the polymer may contain ammonium salts; the polymer may contain acid salts having cations other than ammonium cation: the polymer may include sodium salts of the acid; the device may be a lubricious, antithrombogenic catheter device capable of substantially maintaining its internal and external diameter when in contact with blood for extended periods; the catheter may be formed of a nonswellable, dimensionally stable material; the catheter may be an angioplastic catheter having an outer diameter of no more than 12 French; the catheter may be adapted for operation in the coronary vascular system; the surface may be a dimensionally stable polymer selected from the group consisting of nylon, "C-Flex", "Percuflex", "Kraton", polyurethane, polyester and polyethylene; the device may be an angioplasty balloon catheter where at least the balloon is coated; the device may be a guide wire; the device may have a coefficient of friction of 0.1 or less; the lubricious and antithrombogenic coating may be about 1.0 to 10 microns thick when dry; the coating may be about 2 to 5 microns thick when dry; the coating may increase in thickness by about a factor of six to ten when wet; the thickness of the coating may be about 20 microns thick when wet; the coating may include a polymer with a molecular weight from about 200,000 to 5,000,000 selected from the group consisting of polyacrylic acid, crotonic acid, maleic acid and amino acids and their derivatives and copolymers; the ammonium cation may be the benzalkonium cation formed by dissociation of benzalkonium chloride.

The present invention provides improved catheters and guidewires and, in general, a coating technique that produces a lubricious and antithrombogenic effect.

DESCRIPTION OF THE PREFERRED EMBODIMENT

First we briefly describe the figures.

BRIEF DESCRIPTION OF THE DRAWINGS

FIG. 1 is a schematic view of a medical device, i.e. an angiographic catheter, coated according to the invention and positioned in a vascular lumen.

FIG. 1a is an enlarged axial cross-section of the catheter of FIG. 1.

FIG. 1b is a section of the catheter taken in the region 1b—1b of FIG. 1a, greatly enlarged.

STRUCTURE

Figure 2:
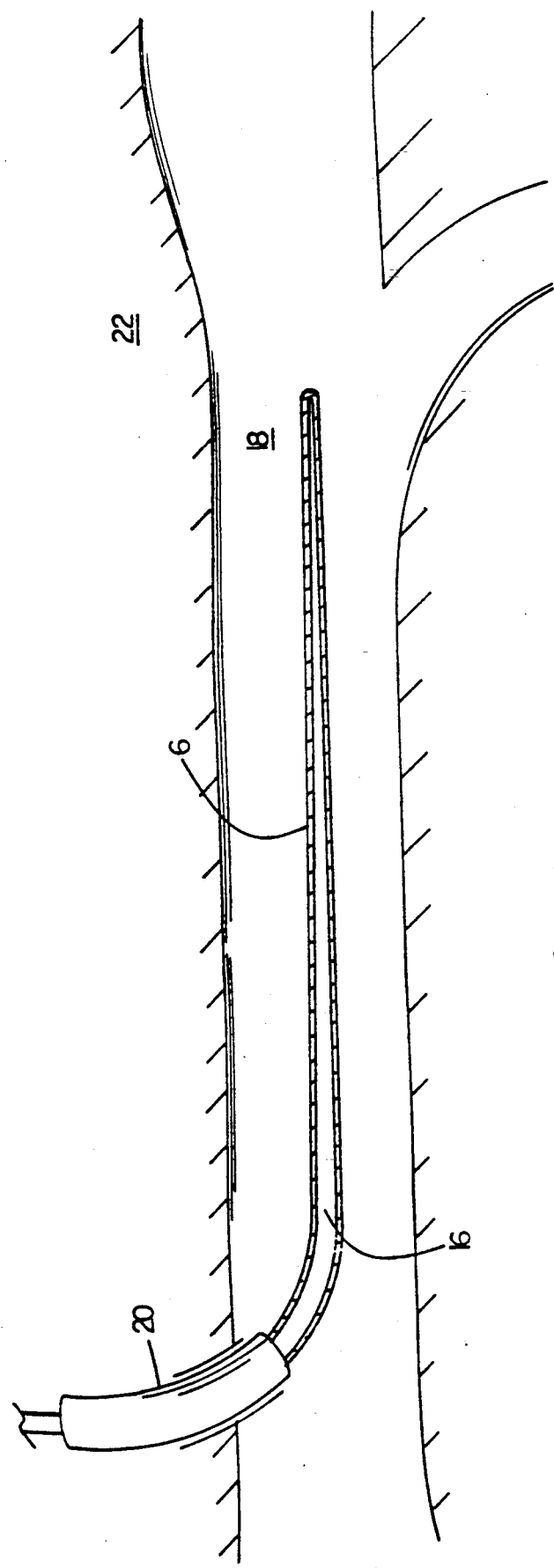
FIG. 2 is a schematic view of a guidewire, coated according to the invention and positioned in a body lumen.

Referring to FIGS. 1-1b, an angiographic catheter 2 of the invention is shown within a tortuous, narrow blood vessel. The catheter 2 is adapted to be positioned in the body by standard catheter procedures, for example, within a blood vessel or the heart, by guiding the flexible catheter through various blood vessels along a circuitous path, starting, for example, by percutaneous introduction through an introducer sheath 7 disposed in a puncture opening of the femoral artery 4. An interior lumen 14 (FIG. 1a) is provided in the catheter for introduction and removal of various medical instruments such as guidewires, endoscopes, ultrasonic imaging equipment and the like.

The surfaces of the catheter 2 which are in communication with the body lumen are provided with coating 6 that is hydrophilic (wettable), a hydrogel (water swellable) and lubricious (low coefficient of friction), for atraumatic advance through the lumen, and highly antithrombogenic to avoid clotting. The inner diameter, $d_1$, remains substantially constant because of the stability of the solid resin that comprises the main body 10 of the catheter; the lumen is unaffected by swelling from contact with blood so that medical operations requiring introduction and withdrawal through the catheter lumen are unaffected. The outer diameter, $d_2$, is also substantially constant, and is only slightly affected by swelling of the coating 6 from contact with blood so that introduction into narrow vascular lumens and blood flow around the catheter is also substantially unaffected by increased diameter. Further, the catheter remains lubricious, antithrombogenic and dimensionally stable even when in contact with blood for extended periods so that operation within a blood vessel can be carried out for a long time, e.g. over 30 minutes, without appreciable clot formation.

Catheters of the invention are particularly suited for introduction into the coronary and peripheral vascular systems where catheterization may take 30 minutes or more and a catheter O.D. (outer diameter) of about 4 to 10 French is required. Operation in the coronary vascular system is also particularly sensitive to maintenance of blood flow and the O.D. of the catheter therefore must be dimensionally stable.

The catheter 2 includes a relatively thin coating 6 bonded to the catheter body surfaces. In the figures, the relative thickness of the coating 6 is greatly exaggerated for clarity. When dry, the coating of the invention is preferably of the order of about 1.0 to 10 $\mu$m thick, a 2 to 5 microns ($\mu$m) coating is typical. Very thin coatings, e.g., of about 0.2–0.3 $\mu$m (dry) and much thicker coatings (e.g. more than 10 $\mu$m dry) are also possible. The coatings are a hydrogel, i.e., they are hydrated in the presence of water, and swollen such that the film may be composed of a greater percentage of water by weight than polymer. Typically, the coating thickness may swell by about a factor of about six to ten or more when the coating is hydrated. For example, a coating of about 1 to 3 $\mu$m thickness, when dry, usually swells to about 10-30 $\mu$m thickness when hydrated. Coatings which are too thick, usually over about 10 $\mu$m dry, are not suitable for some applications since they may crack or flake off a flexible surface and when swelled, may be more easily rubbed off the substrate, such as a catheter during passage through a tortuous lumen. In the example of FIGS. 1-1b, only the outer surface 9 of the catheter is coated, however, it will be understood that the inner surface 11 may also be coated or only portions of the surfaces may be coated, as needed.

As shown in enlarged cross-section view, FIG. 1b, the coating 6 includes a lubricious binding component, shown schematically as 8, and an antithrombogenic component, shown schematically as 12. The binding component 8 is a hydrophilic, swellable highly lubricious polymer layer having carboxyl groups, (acid groups) with quaternary ammonium cations bonded into the polymer layer. The binding layer 8 acts to bind both the coating to the surface and the antithrombogenic component 12 to the coating.

The antithrombogenic component 12 is an antithrombogenic anion, for example, heparin, which is electrostatically attracted to the quaternary ammonium cations of the binding layer in a manner allowing time release of heparin to inhibit clot formation.

It will be understood that the components 8 and 12 of the coating are shown schematically as discrete layers but the actual composure of the coating is a single, integrated lubricious layer which includes the ammonium cation to which the heparin is attracted. It will also be understood that most of the heparin may be in the outer portions (away from the catheter surface) of the lubricious antithrombogenic coating.

Since the heparin is bound by electrostatic attraction, it may be released gradually and inhibit formation of thrombin for an extended period of time. Since only the thin coating is swellable and lubricious, and bound to the catheter, the main body of the catheter may be made of a dimensionally stable material so that the internal and external diameters are substantially maintained, yet the surfaces are highly lubricious for atraumatic advance in body lumens. The thinness of the coating 6 also helps to accomodate bending or other deformation of the main body without fracture or harm to the coating.

Figure 3:
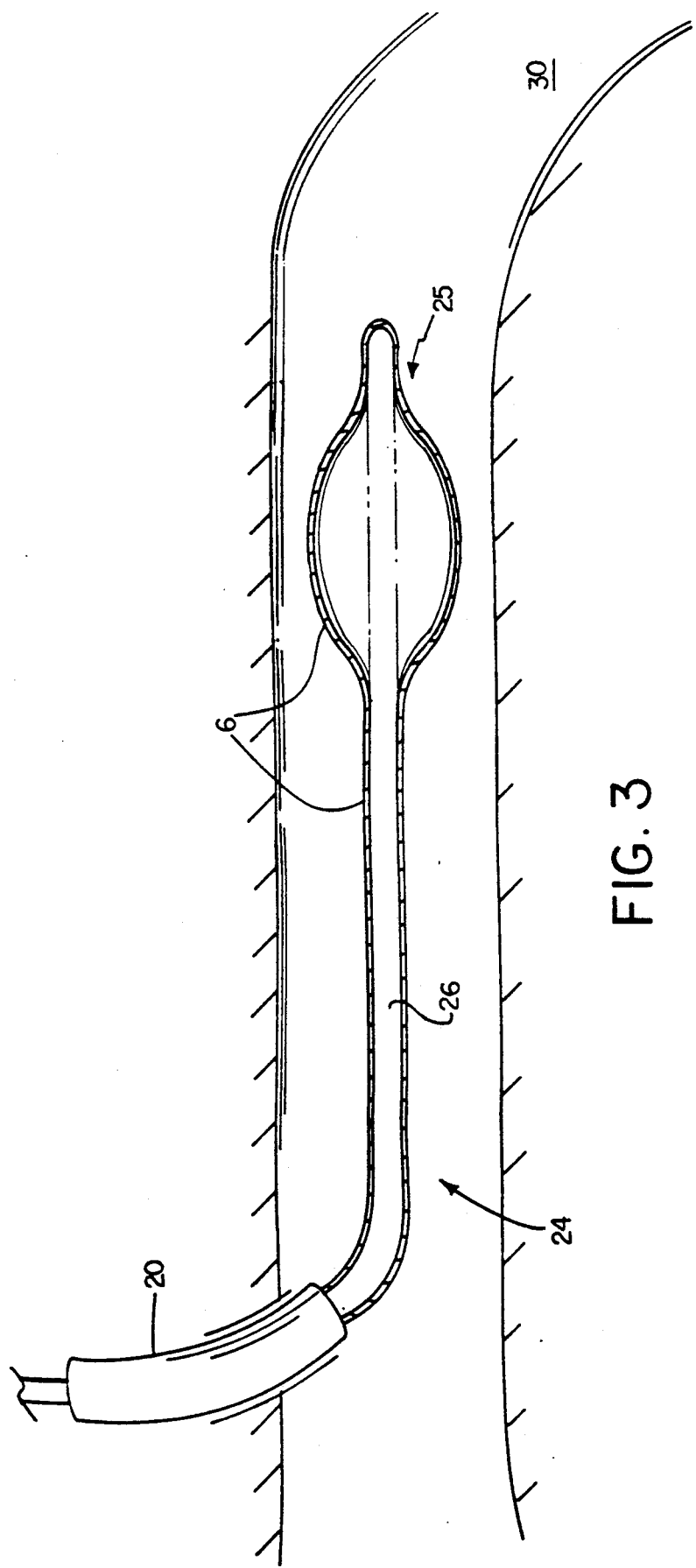
FIG. 3 is a schematic view of a balloon catheter coated according to the invention and positioned in a body lumen.

Referring to FIG. 2, a guidewire 16 having a swellable, lubricious and antithrombogenic coating 6 (greatly enlarged) can be used, for example, for treatment of vascular ailments. Generally, a physician inserts the distal end of guidewire 16 into a body lumen 18 such as a blood vessel. The guidewire 16 is inserted using, for example, the Seldinger technique, through an introducer sheath 20, placed in a limb 22, like the leg, to give access to the lumen 18, e.g., the femoral artery. Axial pressure is applied to the proximal portion, e.g., to advance the guidewire 16 in the lumen. In FIG. 3, an angioplasty balloon catheter 24 having a catheter 26 and a balloon 25 is shown in a tortuous artery 30. The balloon 25 may be inflated to dilate the artery by, for example, the application of pressure and/or heat. The balloon 25 and the catheter 26 (or, for example, Just the catheter 26) include a coating 6 as described. For both the guidewire (FIG. 2) and the balloon catheter (FIG. 3), the lubriciousness of the coating facilitates positioning in tortuous body lumens while the antithrombogenicity inhibits clotting.

In a particular method of forming the coating, the binding component of the thin film is formed on a substrate. A lubricious, hydrophilic, water-swellable, acid-containing polymer, for example, polyacrylic acid is reacted with the binding component. The coefficient of friction of a polyacrylic acid coating, when wet, is generally about 0.02μ. A quaternary ammonium salt, for example a quaternary ammonium halide salt, is then applied to the polymer acid surface to neutralize acid moieties of the polyacrylic acid polymer. The surface is then dried. Heparin is applied to the catheter. The coefficient of friction of the catheter, after heparinization and when wet, is generally about 0.4 to 0.6. Finally, and optionally, the coefficient of friction of the catheter can be reduced by dipping in a buffer solution, preferably a sodium bicarbonate buffer solution, of about neutral pH. After treatment with the buffer, the coefficient of friction is generally about 0.03 to 0.07. Heparin and the quaternary ammonium salt may also be applied in a single solution. The buffer treatment can also be carried out, for example, prior to application of a single heparin-quaternary ammonium cation solution or after application of a quaternary ammonium cation solution and prior to application of a heparin solution.

The coatings of the invention may be applied to the surface of any material. For angiographic catheters, for example, it is best to use a dimensionally stable catheter material, as discussed, that does not swell in the presence of aqueous solution and maintains its strength and flexibility characteristics. It is also important in angiography that the catheter maintain its inner lumen diameter. Catheters may be formed of, for example, polyurethane, polyester, nylon, C-Flex TM, Percuflex TM, Kraton TM, or polyethylene polymers. Other materials are known and may be similarly employed in angiography and other subcutaneous techniques, for example, metallic guidewires (FIG. 2) and polymer coated metallic guidewires (e.g. "Teflon" coated wires or guidewires coated with various hydrogels) may be coated as taught herein.

The polymer is, for example, polyacrylic acid, but it will be recognized that other polymeric acids might be used, for example polymers and copolymers of amino acids, maleic acid, ethylene maleic acid copolymer, crotonic acid and their derivatives. Preferably the acid polymer has a molecular weight in the range from about 200,000 to 5,000,000.

For bonding the lubricious acid-containing polymer to a surface, several techniques may be used. For example, polyacrylic acid may be grafted onto a surface by coating the surface with the monomer and polymerizing by electron bombardment. This technique is discussed by J. W. A. Ramsey et al. in *British Journal of Urology* (1986), 58. 70–74. Another method for bonding a lubricious polymer is to activate the surface with an isocyanate and bond the isocyanate to a maleic anhydride copolymer, e.g. as disclosed in Terumo EP Application No. 85106929.4. For coating as desribed herein, the maleic anhydride copolymer is contacted with water to form acid groups.

In a particular embodiment of this invention, a polyisocyanate primer is first applied to a surface to be coated and the carboxyl-containing polymer applied to the polyisocyanates. This method is disclosed in "Improved Hydrophilic Lubricious Coating for Medical Devices", U.S. patent application Ser. No. 297,331, filed Jan. 31, 1989, now abandoned, the contents of which are incorporated herein by reference.

For incorporating an ammonium cation, a quaternary ammonium salt is preferably applied to the acid-containing polymer. In one embodiment, benzalkonium cation formed by dissolution of benzalkonium chloride in aqueous solution is used. Phosphonium salts or sulfonium salts might also be employed.

The buffer solution is preferably a biocompatible buffer in a pH range from about 6.5 to 7.5. In one embodiment, a 0.1N sodium bicarbonate buffer is used. Other possible buffers are buffer solutions including sodium diphosphate and sodium monophosohate, sodium hydroxide, potassium hydroxide, ammonium hydroxide, as well as buffers of low molecular weight amines, alkanolines and other low molecular weight catonic species.

It will be realized that the thin, lubricious, antithrombogenic coating of the invention is applicable to a variety of medical instruments other than catheters which require substantial dimensional stability, lubricity and antithrombogenicity.

EXAMPLES

The invention will be further described by way of the following examples 1 to 3. Other examples for bonding an acidic hydrophilic coating to a substrate are given in U.S. patent application Ser. No. 297,331, now abandoned, incorporated, supra. These may also be treated as described herein to impart antithrombogenicity.

EXAMPLE 1

A coating may be formed as follows. The surface of an angiographic catheter to be coated, formed of Nylon 11, is first prepared by wiping down with clean cloth. The catheter has an O.D. (outer diameter) of about 5 French (about 1.88 mm) and an I.D. (inner diameter) of about; 0.040 inch. The catheter is coated in a solution of 4,4' diphenylmethane diisocyanate (MDI) in methylethylketone for 30 minutes. After drying in an air oven at 85° C. for 30 minutes, the catheter is dipped in a 1.7% solution of poly(acrylic acid) homopolymer having a molecular weight of about 3,000,000 in dimethylformamide (DMF) and tertiarybutyl alcohol. After redrying at 85° C. for 30 minutes, a smooth coating is obtained. The catheter is oven dried for 8 hours at 50° C. One function of the drying steps is to remove solvent from the coating. The surface of the catheter becomes instantly lubricious upon exposure to water.

The polyisocyanate solution is at a concentration of about 0.5 to 10% by weight. The polyacrylic acid is at a concentration of about 0.1 to 10% by weight. The poly(carboxylic acid) to polyisocyanate molar ratio is generally about 1:1.

The hydrophilic surface is rinsed with distilled water. A benzalkonium chloride solution (Benzalkonium Chloride available from Aldrich Chemical, Milwaukee, Wis.) is next applied by dipping. The aqueous solution typically has a concentration of 1-2% by weight (pH of about 5 to 7) and the catheter is dipped for 5 minutes at room temperature, followed by a 5 minute rinse in distilled water. The catheter is then air dried. In the addition of the amonium cation solution, we believe, quaternary ammonium salts of the hydrophilic acid polymer are formed.

A solution of a heparin salt is applied to the coating. The solution is 10,000 units heparin sodium injection (Fisher Scientific, Pittsburg, Pa.) USP Grade (1,000 units/ml which is then added to 650 cc distilled water) and is applied by dipping for 5 minutes at room temperature. The heparin anions are attracted by the bound ammonium cations and thereby are electrostatically bound into the lubricious coating. The catheter may be air dried and used in contact with blood with high lubriciousness and low thrombogenicity.

EXAMPLE 2

The same procedure as in example 1 may be followed for coating a stainless steel guidewire with a primer solution composed of a 1% polyisocyanate, being an isocyanate end-capped aliphatic prepolymer having an average NCO equivalent weight of 350 and a solution viscosity of about 1000 cps at 25° C. The polyisocyanate is in a solution of methylethylketone. A topcoat solution composed of 1% poly(acrylic acid) (USP grade polyacrylic acid homopolymer of molecular weight about 3,000,000) and 0.5% of MYRJ 53 (nonionic surfactant) in DMF is applied thereafter. The drying cycles for the two coats are 30 minutes at 70° C. and 30 minutes at 60° C., respectively. The finished stainless steel guidewire shows a lubricious surface upon exposure to water. The quaternary ammonium cation and heparin anion are thereafter applied as in example 1.

EXAMPLE 3

A coating may be applied to an angiographic catheter as in Example 1 or a guide wire as in Example 2. The coefficient of friction when wet is typically about 0.4 to 0.6 after addition of heparin.

The coefficient of friction can be reduced by the following procedure. After heparinization the coated object is dipped in a buffer solution for about 1-2 seconds and generally less than 10 seconds. The buffer is a 0.1N sodium bicarbonate solution. The pH of the buffer is about 7 to 7.5. After the dipping, the catheter is air dried until dry to the touch. Upon rehydration the coefficient of friction, typically, is in a range from about 0.03 to 0.07.

We believe that treatment of the coating with a buffer solution results in further dissociation of the carboxyl moieties of polyacrylic acid and neutralization of the acid anion by the formation of sodium salts of the carboxyl groups of polyacrylic acid. In an aqueous solution, for example in body fluids, the sodium salts are more likely to attract water molecules than would be the free acid. A more hydrogel-like and lubricious coating is achieved.

Other examples for forming acidic polymer coatings on various substrates such as C-Flex TM, Percuflex TM, Kraton TM, and poly(ethylvinylacetate) are disclosed in U.S. patent application Ser. No. 297,331, now abandoned, which may be used for forming an antithrombogenic coating by the method of Example 1.

ANTITHROMBOGENIC TEST DATA

The procedure used to test the antithrombogenic nature of catheters coated according to the invention will now be described.

Four mongrel dogs (20–25 kilograms) were used for this test. The technique is described in "A New, Simple Test for Thrombogenity", *Radiology*, 120:53–55, 1976, was utilized. The animals were anesthetized with sodium pentobarbital (30 milligrams/kilogram). The catheters used were formed of Nylon 11.

The catheter tests used simultaneous bilateral cutdowns of the jugular veins, femoral veins, carotid arteries and femoral arteries. In sequential bilateral pairs, catheters were introduced utilizing the Seldinger technique. Six inches of catheter were advanced into each vessel. Catheters were closed with a stopcock and secured in place to prevent migration.

After 45 minutes from the time of placement of the last pair of catheters, the dogs were fully heparinized and euthanized. Catheters were retrieved enbloc by resection of the respective vessels. The vessels were incised longitudinally, the catheters were removed and the clot adherent was weighed. The filter and collection apparatus were washed in tap water. The clots were placed on a filter paper and weighed to 0.001 milligram. Simultaneous testing was carried out with hydrophilic versus non-coated control catheters in two animals and the remaining comparison study as discussed below was carried out in one animal each.

Figure 4:
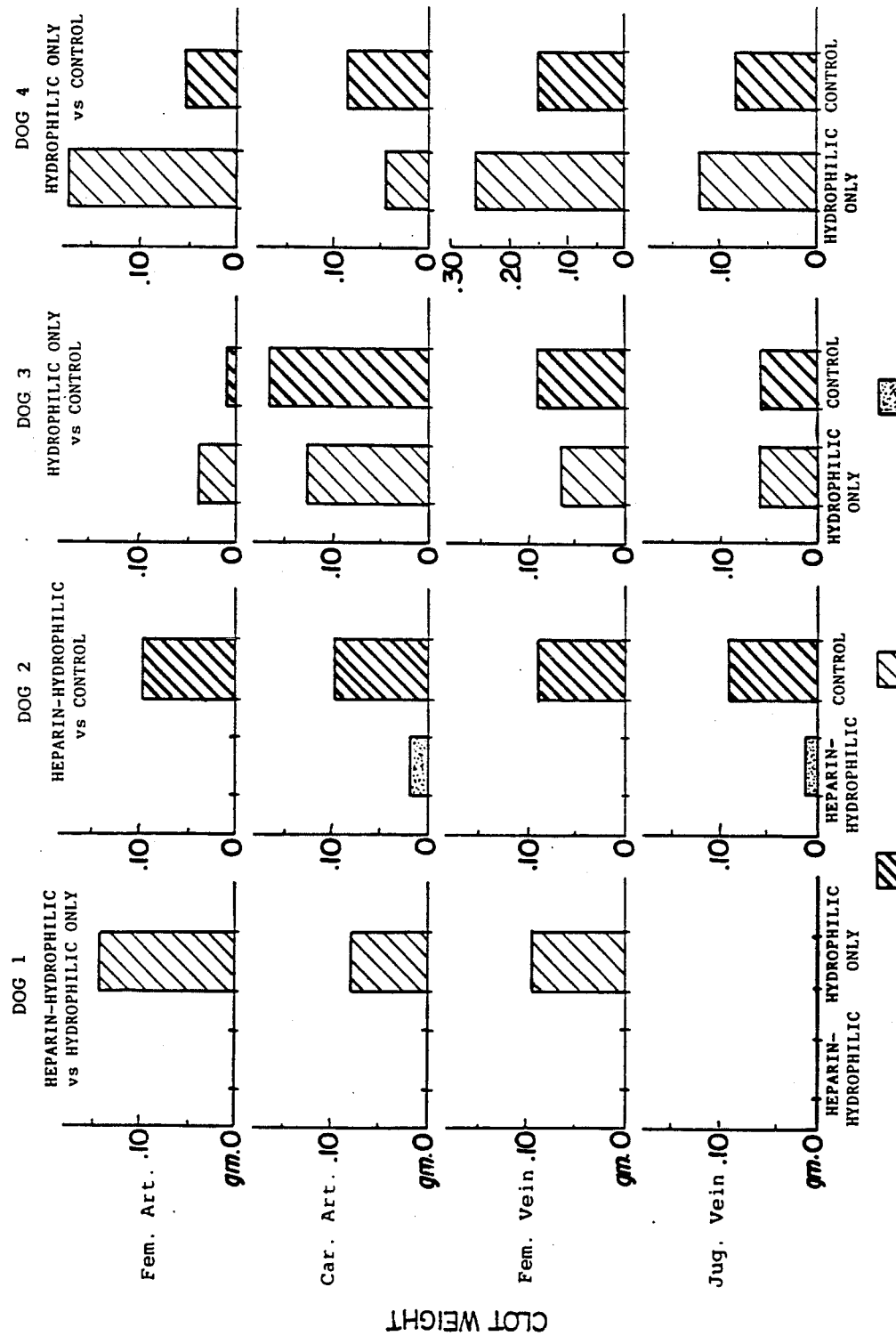
FIG. 4 is a bar graph depiction of test data comparing the antithrombogenic effect of an uncoated surface, a surface coated with a hydrophilic polymer and an antithrombogenic polymer surface according to the invention.

Mean clot weight and standard deviations are displayed graphically in FIG. 4. Catheter pairs tested include: dogs 3 and 4, non-coated (control) vs. hydrophilic coating only (isocyanate-polyacrylic acid coating prior to addition of ammonium cation); dog 2, noncoated vs. heparinized-hydrophilic (prepared as described in Example 1); and dog 1, heparinized-hydrophilic vs. hydrophilic only.

As the results clearly show, the coatings of the present invention have increased the antithrombogenicity. For dog 1, no weighable clot was formed on catheters coated with the heparinized-hydrophilic coating whereas hydrophilic coatings without heparinization can induce appreciable clotting. For dog 2, the results are similar. Only a small amount or no clot was detectable with the heparinized-hydrophillic coating whereas the noncoated catheter produced appreciable clotting. Dogs 3 and 4 show similar clot formation using an uncoated catheter and a catheter coated with a hydrophylic coating.

Furthermore, the hydrophilic-heparinized catheters had enhanced antithrombogenic effect for time periods of at least 45 minutes. Similar results can be obtained when the coatings are treated with buffer to enhance lubricity.

The heparinized-hydrophillic coatings also impart high lubricity when applied, for example, to catheters and guidewires, which facilitates manipulation and makes them very useful angiographic tools. As discussed, the coefficient of friction of the coatings in aqueous solutions prior to addition of heparin (after addition of ammonium cation) is typically 0.02 as compared with Teflon ® which is 0.10 and after heparinization, about 0.4 to 0.6. With further neutralization by buffer treatment the coefficient of friction is about 0.02 to 0.07.

It will be understood by those skilled in the art that many variations of the teachings above may be implemented without departing from the spirit and scope of the present invention.

We claim:

1. Method for rendering a surface of a preformed article lubricious and antithrombogenic comprising:
   providing on said surface a thin coating of biologically compatible, lubricious, hydrophilic polymer including acid groups, and thereafter applying to said coating ammonium cation, heparin and buffer solution in the manner that heparin is bound by electrostatic attraction to ammonium cation of said coating to permit time release of heparin in the presence of body fluid, and said buffer solution acts to enhance lubriciousness of said coating.

2. Method for rendering a surface of a preformed article lubricious and antithrombogenic comprising:
   providing on said surface a thin coating of biologically compatible, lubricious, hydrophilic polymer including acid groups, and thereafter applying to said coating ammonium cation and heparin in the manner that heparin is bound, by electrostatic attraction to ammonium cation of said coating to permit time release of heparin in the presence of body fluid, the thickness of said lubricious and antithrombogenic coating being of the order of about 10 microns or less when dry.

3. The method of claims 1 or 2 further comprising:
   applying to said lubricious polymer coating ammonium cation and heparin, and, thereafter applying buffer solution.

4. The method of claim 3 wherein ammonium cation is applied before heparin is applied.

5. The method of claims 1 or 2 further comprising: applying to said lubricious polymer coating ammonium cation, applying buffer solution and thereafter, applying heparin.

6. The method of claims 1 or 2 further comprising applying to said lubricious polymer coating, buffer solution and thereafter applying ammonium cation and heparin.

7. The method of claims 1 or 2 wherein ammonium cation is provided by applying an aqueous solution.

8. The method of claims 1 or 2 further including drying said polymer coating after applying ammonium cation.

9. The method of claims 1 or 2 further including drying said coating before providing buffer solution.

10. The method of claims 1 or 2 wherein buffer solution of sodium bicarbonate buffer is applied to said coating to enhance lubriciousness.

11. The method of claims 1 or 2 comprising applying buffer solution to enhance lubriciousness by formation of salts of said acid groups.

12. The method of claims 1 or 2 comprising reducing the coefficient of friction of said coating by applying a buffer solution wherein after applying said buffer solution said coefficient of friction is less than about 0.1.

13. The method of claims 1 or 2 wherein said providing lubricious polymer includes:
   providing to said surface a primer solution including isocyanate and providing a hydrophilic polymer coating to said isocyanate.

14. The method of claims 1 or 2 wherein said hydrophilic polymer has a molecular weight from about 200,000 to 5,000,000 and is selected from the group consisting of polyacrylic acid, crotonic acid, maleic acid and amino acids and their derivatives and coploymers.

15. The method of claims 1 or 2 wherein said preformed surface is selected from the group consisting of nylon, polyurethane, polyester, "C-Flex", "Percuflex", "Kratón", and polyethylene.

16. The method of claims 1 or 2 wherein said ammonium cation is benzalkonium cation formed by dissociation of benzalkonium chloride.

17. The method of claims 1 or 2 wherein said ammonium cation is provided in a manner causing reaction of said cation with acid groups to form ammonium salts.

18. The method of claims 1 or 2 wherein said polymer and heparin are applied in the manner to provide a coating which is about 1.0 to 10 microns thick, when dry.

19. The method of claim 18 wherein said coating is about 2 to 5 microns when dry.

20. The method of claims 1 or 2 wherein the thickness of said coating increases by about six to ten times when wet.

21. The method of claims 1 or 2 wherein the thickness of said coating is about 20 microns when wet.

22. The method of claims 1 or 2 wherein said coating is applied to an angioplastic catheter.

23. The method of claims 1 or 2 wherein said coating is applied to angioplasty balloon catheter.

24. The method of claims 1 or 2 wherein said coating is applied to a guidewire.

25. The method of claim 24 wherein said guidewire is a polymer coated guidewire.

26. A medical device for use within the body formed of a dimensionally stable base material forming the main body of said device and having a thin lubricious coating on its surface, said coating being capable of reducing the thrombogenicity of said surface and comprising:

a lubricious, hydrophilic, swellable polymer, being on said surface said polymer having covalently bonded acid groups, and incorporating noncovalently bonded ammonium cations, and heparin bound in a manner permitting time release in the presence of body fluid, the thickness of said lubricious and antithrombogenic coating being of the order of 10 microns or less when dry.

27. A medical device for use within the body formed of a dimensionally stable base material forming the main body of said device and having a thin lubricious coating on its surface, said coating being capable of reducing the thrombogenicity of said surface and comprising:

a lubricious, hydrophilic, swellable polymer being on said surface, said polymer having covalently bonded acid groups and incorporating noncovalently bonded ammonium cations, and heparin bound in a manner permitting time release in the presence of body fluid, and acid salts to enhance lubricity.

28. The device of claims 26 or 27 wherein said polymer contains ammonium salts.

29. The device of claims 26 or 27 wherein said polymer contains acid salts having cations other than said ammonium cation.

30. The device of claims 26 or 27 wherein polymer includes sodium salts of said acid.

31. The device of claims 26 or 27 comprising a lubricious, antithrombogenic catheter device capable of substantially maintaining its internal and external diameter when in contact with blood for extended periods said catheter being formed of a nonswellable, dimensionally stable material.

32. The device of claim 29 wherein said catheter is an angioplastic catheter having an outer diameter of no more than 12 French.

33. The device of claim 29 wherein said catheter is adapted for operation in the coronary vascular system.

34. The device of claims 26 or 27 wherein said surface is a dimensionally stable polymer selected from the group consisting of nylon, "C-Flex", "Percuflex", "Kraton", polyurethane, polyester and polyethylene.

35. The device of claims 26 or 27 comprising an angioplasty balloon catheter wherein at least the balloon of said catheter is coated.

36. The device of claims 26 or 27 comprising a guide wire.

37. The device of claim 36 wherein said guidewire is a polymer coated guidewire.

38. The device of claims 26 or 27 having a surface of coefficient of friction of 0.1 or less 39. The device of claims 26 or 27 wherein said coating is about 1.0 to 10 microns thick when dry.

40. The device of claim 37 wherein said coating is 2 to 5 microns thick when dry.

41. The device of claims 26 or 27 wherein said coating increases in thickness by about a factor of six to ten when wet.

42. The device of claims 26 or 27 wherein said coating is about 20 microns when wet.

43. The device of claims 26 or 27 wherein said coating includes a polymer with a molecular weight from about 200,000 to 5,000,000 selected from the group consisting of polyacrylic acid, crotonic acid, maleic acid and amino acids and their derivatives and copolymers.

44. The method of claims 26 or 27 wherein said ammonium cation is the benzalkonium cation formed by dissociation of benzalkonium chloride.

45. A medical device for use within the body formed of a dimensionally stable base material forming the main body of said device and having a thin lubricious coating on its surface, said coating being capable of reducing the thrombogenicity of said surface and formed by the process comprising:

providing on said surface a thin coating of biologically compatible, lubricious, hydrophilic polymer including acid groups, and thereafter applying to said coating ammonium cation, heparin and buffer solution in the manner that heparin is bound by electrostatic attraction to ammonium cation of said coating to permit time release of heparin in the presence of body fluid, and said buffer solution acts to enhance lubriciousness of said coating.

46. A medical device for use within the body formed of a dimensionally stable base material forming the main body of said device and having a thin lubricious coating on its surface, said coating being capable of reducing the thrombogenicity of said surface and formed by the process comprising:

providing on said surface a thin coating of biologically compatible, lubricious, hydrophilic polymer including acid groups, and thereafter applying to said coating ammonium cation and heparin in the manner that heparin is bound, by electrostatic attraction to the ammonium cation of said coating to permit time release of heparin in the presence of body fluid, the thickness of said lubricious and antithrombogenic coating being of the order of about 10 microns or less when dry.

47. The invention of any one of claims 1, 2, 26, 27, 45 or 46 wherein said polymer is polyacrylic acid.

48. The invention of claim 47 wherein said surface is a metal surface.

* * * * *